United States Patent [19]

Rhoades et al.

[11] 4,338,563

[45] Jul. 6, 1982

[54] CORROSION MEASUREMENT WITH SECONDARY TEMPERATURE COMPENSATION

[75] Inventors: Rex V. Rhoades, Anaheim; James L. Geer, Diamond Bar, both of Calif.

[73] Assignee: Rohrback Corporation, Santa Fe Springs, Calif.

[21] Appl. No.: 177,208

[22] Filed: Aug. 11, 1980

[51] Int. Cl.³ .............................................. G01R 27/02
[52] U.S. Cl. ................................. 324/65 CR; 324/71 R
[58] Field of Search .............. 324/65 CR, 71 R, 71 E; 338/13, 38

[56] References Cited

U.S. PATENT DOCUMENTS

| | | | |
|---|---|---|---|
| 2,565,230 | 8/1951 | Hebler | 73/27 |
| 2,664,543 | 12/1953 | Thayer | 324/20 |
| 2,956,225 | 10/1960 | Marsh et al. | 324/71 |
| 3,042,863 | 7/1962 | Marsh et al. | 324/71 |
| 3,060,728 | 10/1962 | Wolber | 73/86 |
| 3,102,979 | 9/1963 | Schaschl | 324/71 |
| 3,104,355 | 9/1963 | Holmes et al. | 324/71 |
| 3,108,242 | 10/1963 | Scott, Jr. | 338/13 |
| 3,124,771 | 3/1964 | Rohrback | 338/13 |
| 3,148,348 | 9/1964 | Rohrback | 338/13 |
| 3,153,217 | 10/1964 | Cramer et al. | 338/13 |
| 3,155,933 | 11/1964 | Rohrback et al. | 338/13 |
| 3,155,934 | 11/1964 | Messick et al. | 338/13 |
| 3,264,561 | 8/1966 | Gustafson | 324/71 |
| 3,307,401 | 3/1967 | Bachman | 324/71 E |
| 3,331,021 | 7/1967 | Marsh et al. | 324/71 |
| 3,358,229 | 12/1967 | Collins | 324/65 |
| 3,497,803 | 2/1970 | Fegan, Jr. | 324/65 |
| 3,609,549 | 9/1971 | Hausler | 324/65 |
| 3,731,187 | 5/1973 | Hausler | 324/65 |
| 3,821,642 | 6/1974 | Seymour | 324/65 |
| 3,854,087 | 12/1974 | Frenck | 324/65 |
| 3,857,094 | 12/1974 | Caldecourt | 324/65 |
| 3,936,737 | 2/1976 | Jeffries, Sr. | 324/65 |
| 4,019,133 | 4/1977 | Manley | 324/65 |
| 4,138,878 | 2/1979 | Holmes | 73/15 |
| 4,147,513 | 4/1979 | Bienkowski | 23/232 |
| 4,217,544 | 8/1980 | Schmidt | 324/65 |

*Primary Examiner*—Stanley T. Krawczewicz
*Attorney, Agent, or Firm*—Gausewitz, Carr, Rothenberg & Edwards

[57] ABSTRACT

An electrical resistance type corrosion measuring probe has a test element exposed to a corrosive environment and an adjacent reference element protected from the environment. Electrical circuitry is connected to the elements for measurement of resistance ratio. This provides a corrosion output signal having a first order of temperature correction provided by the reference element. Secondary temperature compensation for dynamic or short term variation of temperature of the corrosive environment is provided by thermocouple measurement of temperatures of the test and reference elements and compensating the corrosion signal in accordance with the directly measured short term temperature difference of the elements.

18 Claims, 10 Drawing Figures

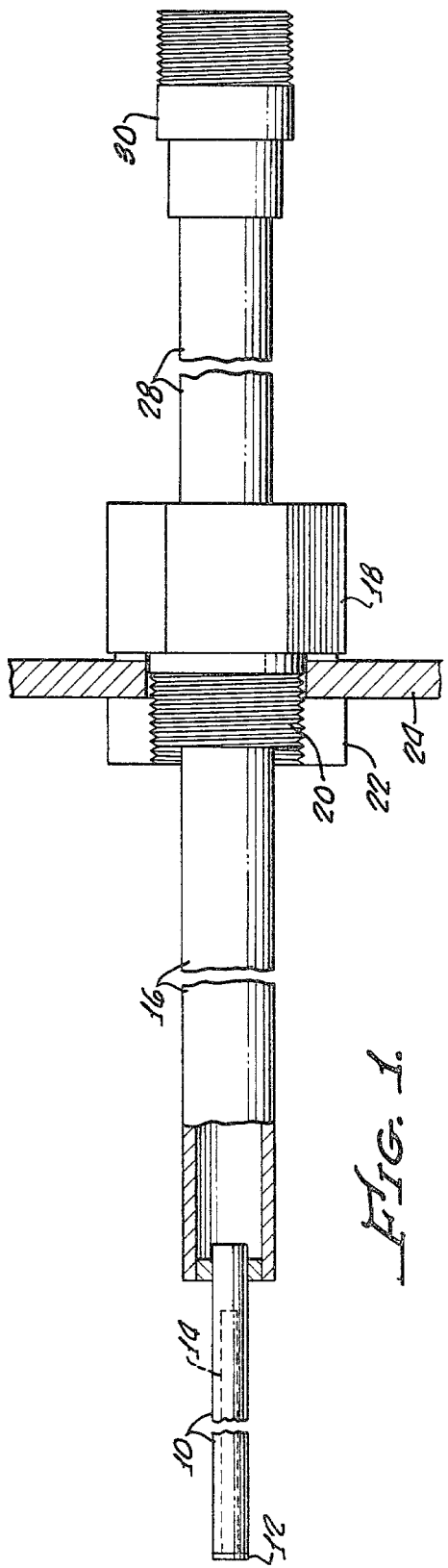
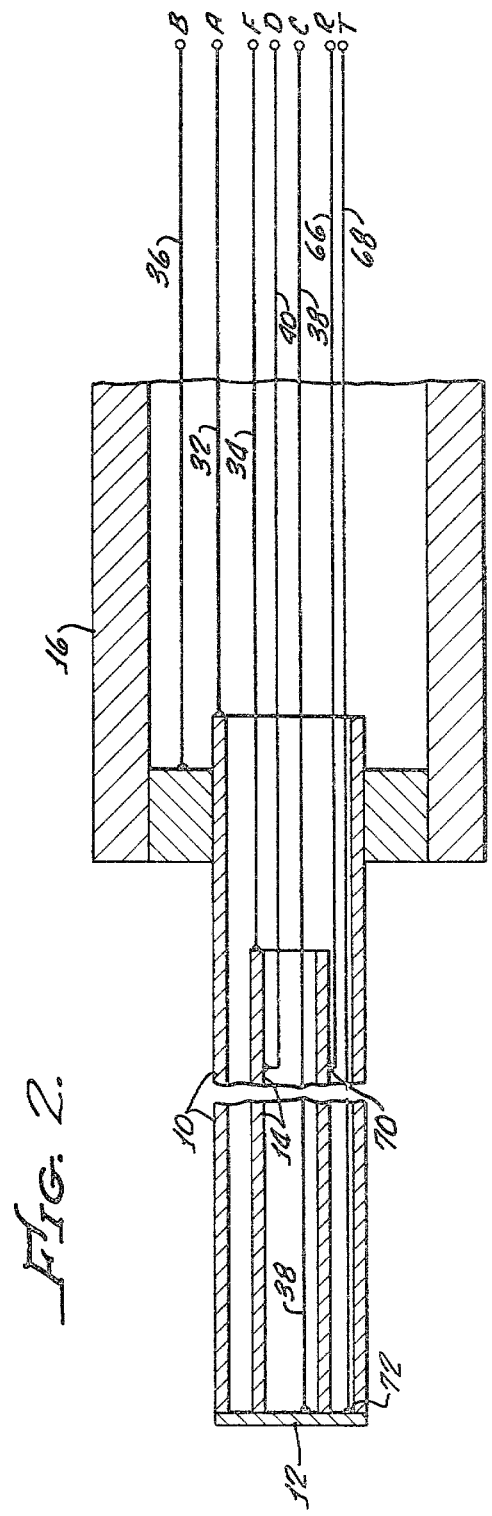
Fig. 1.
Fig. 2.

(a)

(b)

(c)

(d)

TIME

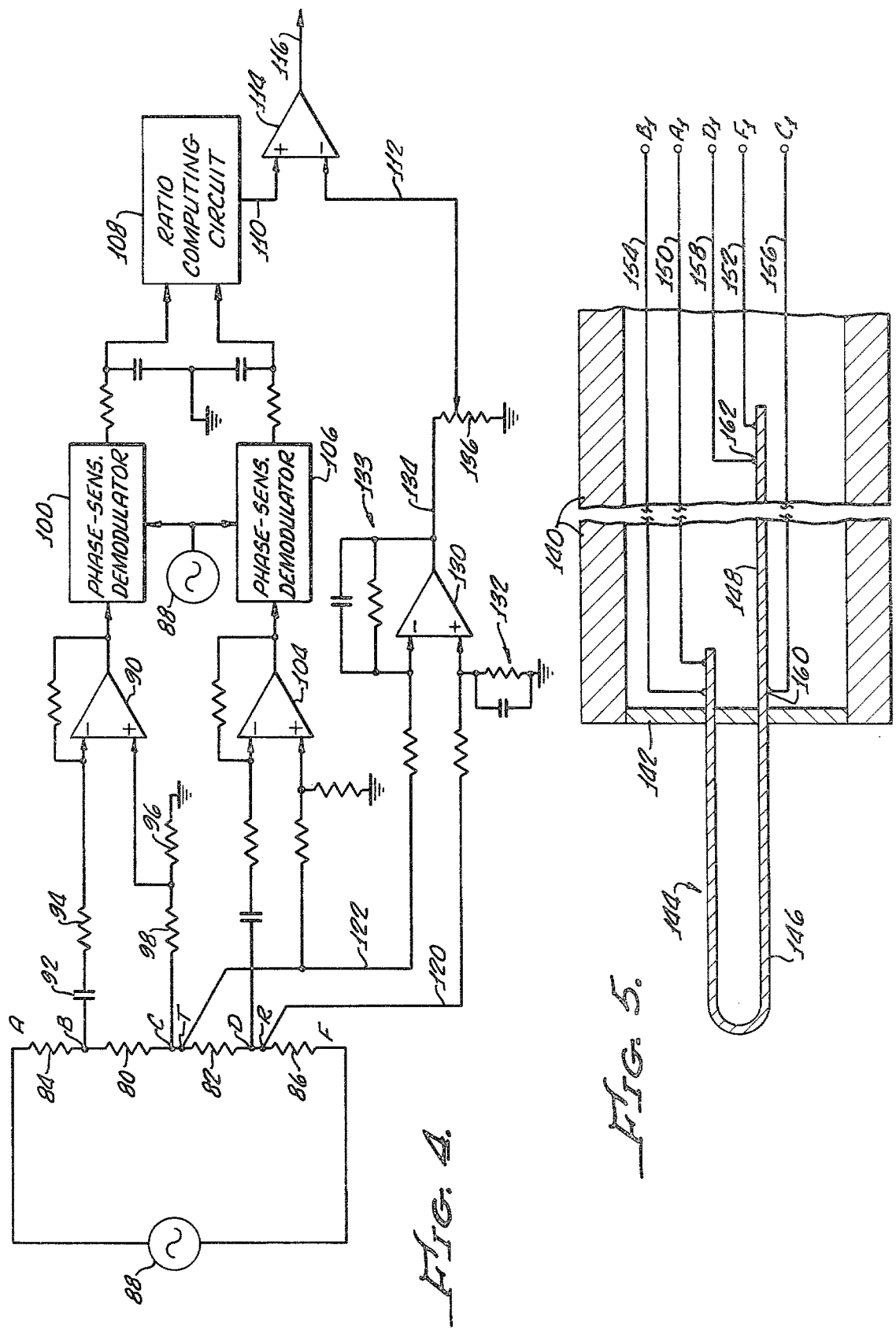

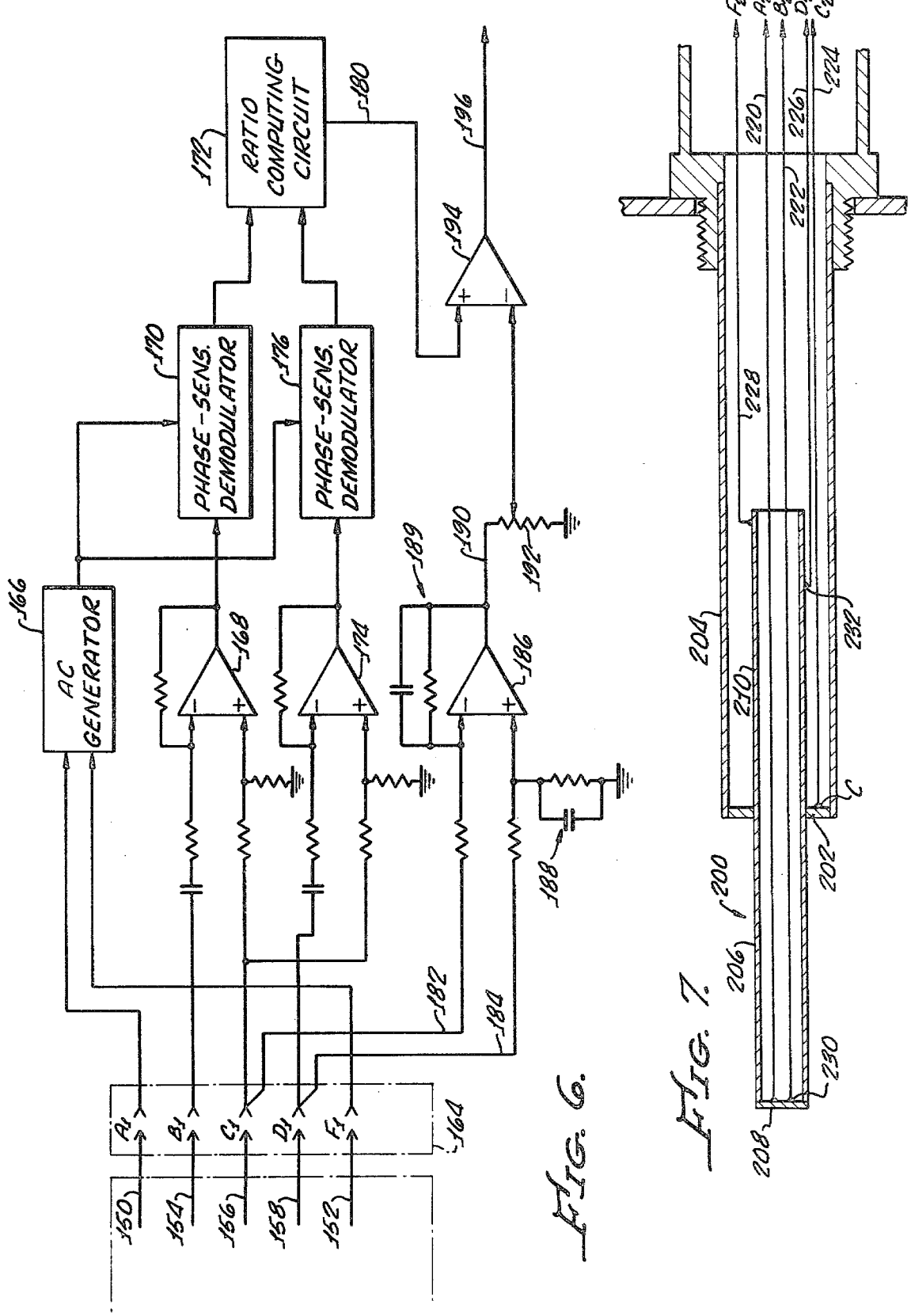

CORROSION MEASUREMENT WITH SECONDARY TEMPERATURE COMPENSATION

BACKGROUND OF THE INVENTION

This invention relates to measurement of corrosive characteristics of a fluid and more specifically concerns improved temperature compensation for such measurement.

A common method of continuous measurement of corrosion characteristics employs resistance measurements of a metallic corrodable test element to indicate, by change in resistance, the amount of metal that has been lost by corrosion over a period of time. A widely used instrument for this measurement is known as a Corrosometer probe manufactured by Rohrback Corporation, assignee of this application. One such probe employs a tubular metallic test element carrying an inner reference element made of the same material as the test element. The interior of the tubular test element is filled with a thermally conductive electrically non-conductive compound. Alternating current is passed through the elements and electrical resistance of each is measured while or after the probe has been immersed in an environment of which corrosive tendencies are to be monitored. Because resistance changes with the amount of metal in the test element, measurement of test element resistance provides an indication of corrosion. However, since resistance of the metal also changes with temperature, a reference element is provided, made of the same material as the test element and having the same temperature resistance characteristic. Thus changes in resistance of the test element that are due to long term, relatively slow temperature variation may be eliminated by comparison of resistances of the test and reference elements.

The described temperature compensation is useful solely for relatively slowly varying or long term temperature fluctuation. Dynamic or short term, rapid temperature fluctuations cause temporary but significant errors in the corrosion signal obtained with the prior long term compensation. This is due, at least in part, to the fact that the reference element, although made of the same material as the test element and placed quite close to the test element, must be protected from the corrosive environment so that the reference element does not corrode. Further, the commonly used electrically non-conductive compound, even though desirably thermally conductive, has a greater thermal resistance than does the metal of the test element. Heat of the external environment is transmitted to the protected reference element largely through this electrically insulative compound. Accordingly, a rapid rise in temperature of the environment in which the probe is immersed will effect a more rapid rate of increase of temperature of the test element than of the reference element. Upon occurrence of rapid changes in environment temperature, change in temperature of the protected reference element lags change in temperature of the unprotected test element. Therefore there is an erroneous reading, caused by this lagging temperature response of the reference element, until the temperatures of the two elements become equalized.

Although the error due to rapidly varying temperature may last for only a relatively short period, should rapid temperature changes recur frequently, the error in corrosion reading will likewise recur frequently. This error of rapid temperature fluctuation is a problem when attempting to measure corrosion in a system wherein the temperature is not held constant, a problem of increasing significance as magnitude and rate of temperature fluctuation of the fluid environment increase.

Accordingly, it is an object of the present invention to provide corrosion measurement which eliminates or substantially decreases this problem.

SUMMARY OF THE INVENTION

In carrying out principles of the present invention in accordance with a preferred embodiment thereof, temperature compensation is provided for a corrosion measurement of the type made by measuring resistances of a test element arranged for exposure to a corrosive environment and a reference element protected from the corrosive environment and combining the measured resistances to provide a first order of temperature compensation. A secondary temperature compensation is achieved by sensing temperatures of the test and reference element and employing the difference between such sensed temperatures to compensate the corrosion signal. According to one feature of the invention, difference in temperatures between the test and reference elements is directly measured by thermocouples that employ the same electrical wire conductors that are used for resistance measurement.

BRIEF DESCRIPTION OF THE DRAWINGS

FIG. 1 illustrates certain structure of a corrosion measuring probe that may be employed in practice of the present invention;

FIG. 2 is a schematic illustration of the probe of FIG. 1 showing certain electrical leads connected thereto;

FIG. 4 is one type of electrical circuit for providing secondary temperature compensation;

FIG. 5 is a schematic illustration of a wire-type corrosion probe wherein the electrical leads can be used for measuring both resistance and temperature;

FIG. 6 is a circuit similar to that of FIG. 4 for use with the dual function leads of the probe of FIG. 5; and FIG. 7 illustrates a simplified probe construction.

DETAILED DESCRIPTION

Figure 3:
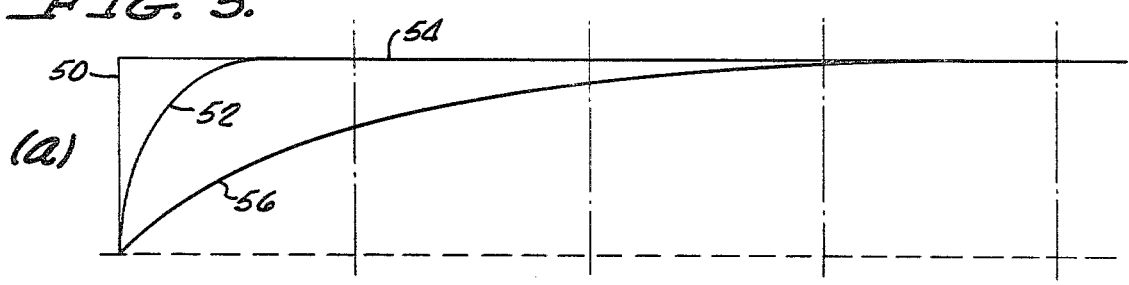
FIG. 3a-d illustrate certain temperature and electric signal variations useful in understanding principles of the invention.
Figure 3:
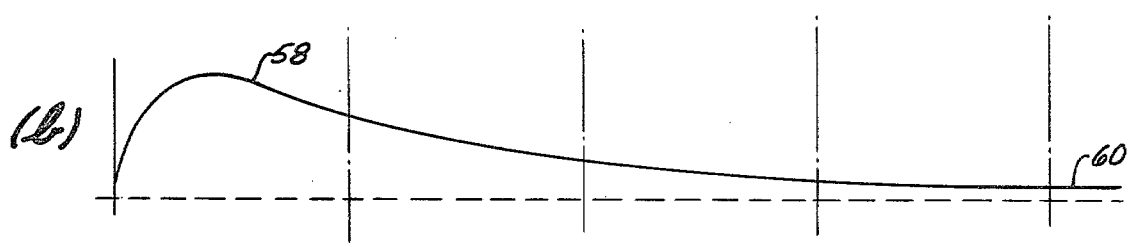
Figure 3:
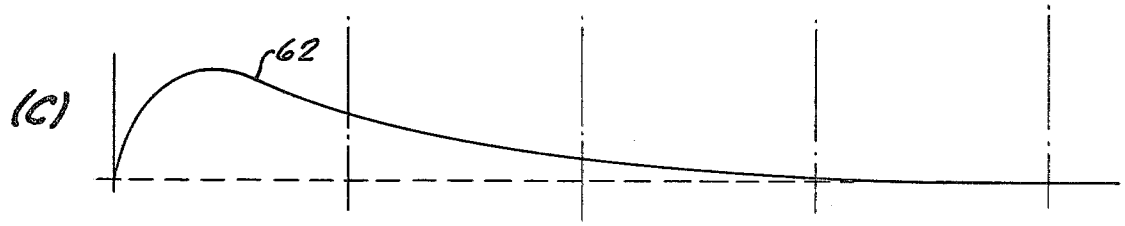
Figure 3:
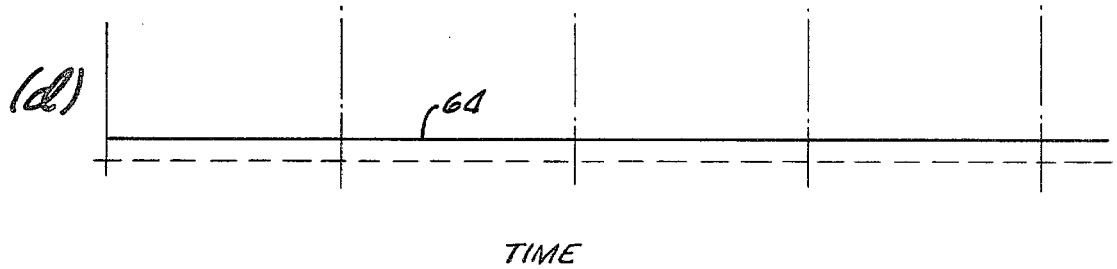

Illustrated in FIG. 1 is a tubular type corrosion probe of the type known as a Corrosometer probe manufactured by Rohrback Corporation. In this probe the test element is a thin outer shell 10 having its outer end closed by a fixedly secured disc 12 to which is also secured an inner or reference element 14 formed from the same material as the outer shell, which may be a mild steel, for example. The two elements are electrically and physically connected by the disc 12 and the shell is filled with an electrically insulative but thermally conductive potting compound such as Sauereisen cement. This compound, though thermally conductive, has far less thermal conductivity than the metal of the test and reference elements.

The tubular assembly of test and reference elements is fixedly mounted to and partially within a probe body 16 having a fitting including a tool receiving head 18 and a threaded neck 20 that is adapted to be threadedly received within a suitable female threaded fitting 22 formed in a wall 24 that confines a corrosive liquid of which corrosive tendencies are to be measured. The probe body has a fixed tubular connector section 28 terminating in a probe electrical connector 30 in which terminate the several wires (to be described below) that are connected to the probe elements and extend through the tubular probe assembly and probe body for connection at the connector 30 to a cable (not shown in FIG. 1) that leads to electrical circuitry to be described below.

Schematically illustrated in FIG. 2 are portions of the probe assembly of FIG. 1 showing the several electrical leads, all made of a conventional conductive material of the type commonly employed in instruments of this type. Leads 32 and 34 are connected to inboard ends of the test element 10 and reference element 14 respectively and extend to terminals A and F of the probe connector 30 where they are connected via a cable (not shown) to a source of AC current. Thus, AC current is supplied through electrical leads 32,34, flowing through the test element, through the electrically conductive header disc 12, and through the reference element 14. Electrical resistance of the test element is measured via leads 36,38 connected respectively to the probe body 16 adjacent the inner end of test element 10 and to the inner surface of the end closure disc or header 12, and terminating at connector terminals B and C, respectively. Electrical resistance of reference element 14 is measured via leads 40 and 38, lead 40 being connected near the inner end of the reference element and to probe connector terminal D.

Resistance of the test element, between terminals B and C, and resistance of the reference element, between terminals D and C, are compared in the conventional and commercial version of the probe to provide a corrosion measurement signal. Such comparison is commonly performed in a circuit (such as a conventional Wheatstone bridge) that computes the ratio of the two resistances. Resistance of the test and reference elements varies with both temperature and corrosion. Therefore, the ratio of the resistance of the reference element to the resistance of the test element provides a corrosion signal compensated for the temperature induced component of measured resistance of the test element. Since the reference element is in close proximity to the test element, it experiences a temperature close to that of the test element and accordingly the resistance of the reference element provides resistance compensation for relatively slow temperature change. Nevertheless, since the reference element is protected from the corrosive environment, which is in direct contact with the outer surface of the tubular test element 10, a rapid change in temperature of the environment causes a rapid change in temperature of the test element, but the change in temperature of the reference element lags this test element change.

A simplified version of this lagging change is illustrated in FIG. 3(a) wherein curve 50 represents a theoretical step increase in temperature of a liquid environment in which the probe is immersed. With such a step change in temperature, the temperature of the outer test element 10 rises rapidly, as indicated by curve 52 and, in one example, may substantially attain the increased level 54 of the environmental temperature within less than one minute. Reference element 14, on the other hand, responds more slowly to the increase in external temperature and its temperature follows curve 56, requiring, in this heuristic example, some three to four minutes to substantially attain the new temperature represented at 54.

As will be more particularly described below, the temperature of the reference element may be offset from that of the test element because of a static thermal gradient between the two under some conditions. Thus the reference temperature, during static conditions of environment temperature, may be slightly offset from that of the test element. In such case the step change of environment temperature, indicated by curve 50, would temporarily increase the offset. The temperature of the reference would then slowly vary until the original (static) offset (not shown in FIG. 3) is regained, but would not be the same as the temperature of the test element.

Since the electrical circuitry provides a corrosion signal in accordance with the ratio between measured resistances of the test and reference elements, and since the resistances are related to temperatures of the elements, the probe output signal of the conventional probe will follow curve 58 as indicated in FIG. 3(b). Curve 58 may be defined as representing the quantity $K(T_t-T_r)$ wherein K is a constant, $T_t$ is temperature of the test element and $T_r$ is temperature of the reference element. As the reference element temperature more closely approaches the temperature of the test element, the difference curve 58 decreases and returns to its previous level, indicated at 60, which is a difference that more accurately reflects actual corrosion of the test element.

In accordance with a feature of the present invention, instantaneous or actual short term temperature difference between test and reference elements is measured. A signal representing this temperature difference, when properly scaled, will appear ideally as the curve 62 of FIG. 3(c), which may be defined as $K_1(T_t-T_r)$ wherein $K_1$ is a scaling or calibrating constant of the temperature difference of the secondary temperature compensation signal. Subtracting a signal representing the temperature difference curve 62 from the corrosion output signal as represented by curve 58, eliminates that component of the corrosion signal caused by the step rise of temperature (curve 50) and yields an output corrosion signal indicated at 64 in FIG. 3(d). The signal of FIG. 3(d) includes both primary and secondary temperature compensation and thus is free of variations caused by rapid temperature fluctuation.

In the arrangement of FIG. 2, temperature measurement of each of the reference and test elements is made by the use of a first thermocouple lead 66 welded to the reference element 14 to provide a first thermocouple junction 70, and a second thermocouple lead 68 welded to the header disc 12, to provide a second thermocouple junction 72. The thermocouple leads are connected respectively at first and second temperature measurement terminals R and T of the probe connector 30. Leads 66,68 are of a material such as Constantan, for example, that is thermoelectrically different than the material of the probe elements. Thus, a thermoelectrically generated voltage difference between terminals R and T is a measure of the temperature difference between junctions 70 and 72. Accordingly, temperatures of the reference and test elements at the thermocouple junctions are measured. The thermoelectrically generated voltage across terminals R and T is a direct measure of the difference in temperature between the test and reference elements.

An exemplary circuit for the probe of FIGS. 1 and 2 is illustrated in FIG. 4 wherein resistor 80 represents the resistance of the test element between the probe connector terminals B and C, resistor 82 represents the resistance of the reference element between probe connector terminals C and D and resistors 84,86 represent resistances of the remaining portions of the probe elements between the points to which the energizing signal from the schematically indicated AC current generator 88 is applied.

The signal across resistor 80 is fed through a test element channel including an operational amplifier 90 having an inverting input indicated by (−), to which probe connector terminal B is coupled via a capacitor 92 and resistor 94, and having a non-inverting input, indicated by (+), grounded through a resistor 96 and connected to probe connector terminal C via a resistor 98. Output of operational amplifier 90 is fed to a phase sensitive demodulator 100, referenced from generator 88, to provide at its output a DC voltage signal having a magnitude that varies with the magnitude of the AC voltage signal across resistor 80, the test element 10. This DC voltage signal is representative of the test element resistance.

A reference element channel includes an operational amplifier 104 receiving at its inverting and non-inverting inputs, respectively, signals from probe connector terminals D and C. The reference element channel is identical to the test element channel and also includes a phase sensitive demodulator 106 providing a DC voltage output having a magnitude proportional to the magnitude of the AC voltage signal across resistor 82, the reference element 14. This DC voltage output is representative of the reference element resistance. Signals at the output of demodulators 100,106 are fed to a ratio computing circuit 108 (which may be a conventional circuit) that combines the two inputs thereto to provide at its output 110 a corrosion signal having the conventional primary temperature compensation. The circuitry described to this point is a simplified version of circuitry of a well known commercially available probe that provides a corrosion signal compensated for slow or substantially static effects of environment temperature upon the output signal. However, as previously described, the corrosion signal on lead 110 is subject to short term or rapid temperature variation errors.

A secondary temperature compensation signal is provided on a line 112 and differentially combined with (subtracted from) the corrosion signal on line 110 in an operational amplifier 114 to provide at the amplifier output 116 the desired corrosion measuring signal. This signal is corrected as in prior devices for static, or slowly changing temperature of the environment and is also corrected for rapid, short term temperature fluctuations.

To obtain the secondary temperature compensation signal on line 112, copper leads 120,122 are connected to terminals R and T, (the probe connector 30 providing a cold junction or isothermal junction between the Constantan and copper leads) and to the respective inputs of a DC operational amplifier 130 having AC signal attenuating filters 132,133 to provide at the amplifier output 134 a DC signal representing difference in temperature between test and reference elements. Thus the AC voltage signal induced by current from the generator passing through resistor 82 is substantially eliminated from the secondary compensation measurement. The temperature difference signal on line 134 is scaled by a variable potentiometer 136 at the wiper arm of which appears the secondary temperature compensation signal, on line 112, that is subtracted from the corrosion signal on line 110.

Potentiometer 136 is adjusted for calibration of the instrument. It is adjusted to vary the magnitude of the secondary temperature compensation signal on line 112 until the corrected corrosion signal output on line 116 exhibits the least change upon occurence of a rapid change in temperature.

The described method and apparatus will compensate not only for difference in temperatures of the resistance test elements due to lagging temperature response of the protected element to a rapid change of temperature, but inherently compensates for a static difference in temperatures between reference and test elements, as mentioned above. Such static temperature difference or temperature offset may be caused by the physical location of the protected element at a point further removed from (for example) the hot liquid environment being sensed and being positioned closer to the lower temperature of the tank wall or external environment. In other words, there may exist a heat gradient from the test element (immersed in the environment being measured) to the reference element (closer to the environment outside of the tank in which the probe is immersed). Further, such temperature offset may vary with the variation of the temperature difference between the interior and exterior of the vessel confining the fluid being monitored. The present invention provides compensation for such temperature offset and for test and reference element temperature differences that may be due to still other factors.

Illustrated in FIG. 5 is a modified form of corrosion probe, generally termed a wire-type probe, in which a tubular probe body 140 has its end sealed by a thin electrically insulative closure disc 142 through which extends a generally U-shaped wire 144 having a test element portion 146, positioned substantially externally of the probe body, and an integral reference element portion 148 within the probe body. The body is filled with an electrically insulative, thermally conductive potting compound and an energizing AC signal is fed via probe connector terminals $A_1$ $F_1$ and leads 150,152 to connections at opposite ends of the wire 144. Resistance of the test element portion 146 is measured between probe connector terminals $B_1$ $C_1$ connected via leads 154,156 to the probe wire 144 on each of the two legs of the wire adjacent the closure disc 142. Resistance of the reference element portion of the wire is measured at probe connector terminals $D_1$ and $C_1$ via leads 158 and 156, the former being connected to an innermost end portion of the protected wire section 148.

In this arrangement secondary temperature compensation is provided by use of the very same wire leads 156,158 and probe connector terminals $C_1$ and $D_1$ that are used to provide the reference element resistance measurement. This is accomplished by forming the leads 156 and 158 of a material that is thermoelectrically different than the metal of the probe element, and measuring the voltage between the two leads. Leads 156,158 may be made of a material such as Constantan, for example. Thus, the junction at point 160 where Constantan lead 156 is welded to the wire body section 148 and also the junction at point 162 where Constantan lead 158 is welded to the wire portion 148, are thermoelectric junctions that form a thermocouple at each of points 160,162. Accordingly the difference in temperature between points 160 and 162 appears as a DC voltage between terminals $C_1$ and $D_1$ (the resistance measurement at these very same terminals being provided by the AC signal as modulated by resistance). Thus leads 156 and 158 are utilized both for the primary resistance measurement of the reference element resistance (in conjunction with measurement of test element resistance) and also for the temperature measurement of the difference in temperatures between reference and test elements.

One of the thermoelectric junctions, junction 162 is positioned at an innermost portion of reference element wire 148, a point where the temperature of this element is affected most slowly by variation of temperature of the environment. The other thermocouple junction, junction 160 is located immediately adjacent the exterior of the probe body 140 and, in effect, directly measures the temperature of the test element portion of the wire portion 146. Measurement of test element temperature may be direct, as by location of a thermocouple, thermocouple junction, thermistor or other temperature sensing device at or on the test element, or such measurement may be made by location of the temperature sensing device on or near some other part of the probe so as to detect temperature of the fluid environment, or of an external part of the probe in contact with the environment, close to the test element.

In the arrangement shown in FIG. 5, additional leads and modification of the probe connector to accommodate additional thermocouple leads from the probe elements are not required for secondary temperature compensation. It will be readily apparent that the use of dual function thermoelectric material leads, as in the probe of FIG. 5, may also be employed in the probe of FIGS. 1 and 2, thus simplifying its construction.

An exemplary electrical circuit for use with the probe of FIG. 5 is illustrated in FIG. 6, showing a probe connector junction 164 in dotted lines. The connector has terminals $A_1$, $B_1$, $C_1$, $D_1$ and $F_1$ connected to leads 150, 154 156, 158 and 152, respectively. It will be understood that all connecting wires other than those designated as being of a thermoelectrically different material, are of conventional electrical lead material and need not be (although they may be) of material thermoelectrically different from that of the test and reference elements. Just as in the previously described embodiment, an AC current generator 166 is connected to terminals $A_1$ and $F_1$ for the probe element resistance ratio measurement. Resistance of the test element, as indicated by the signal across terminals $B_1$ and $C_1$, is measured, as previously described, in a test element channel including an AC operational amplifier 168 having suitable DC eliminating filtering and then fed to a phase sensitive demodulator 170, referenced from the AC generator 166, to provide a test element resistance signal as a first input to ratio computing circuit 172.

In like manner, and as previously described, resistance of the reference element portion of the probe appears as a signal between probe connector terminals $C_1$ and $D_1$ and is fed through a reference element channel including an AC operational amplifier 174, having suitable DC eliminating filtering, and thence to a phase sensitive demodulator 176, also referenced from the AC generator, to provide a second input to the ratio computing circuit 172 at the output of which, on line 180, appears the corrosion signal with its first temperature compensation.

Probe connector junction 164 is the isothermal junction and copper leads 182,184 are connected within this junction to terminals $C_1$ and $D_1$ to which are connected to the thermoelectrically different Constantan wires 156 and 158. The thermoelectrically generated signal on leads 182 and 184 represents the directly measured difference in temperatures between the test and reference elements.

The temperature difference signal on leads 182,184 is a DC signal and is fed to the inverting and non-inverting inputs respectively of a DC operational amplifier 186 which measures the voltage difference between the leads. Amplifier 186 has AC attenuating filter circuits 188 and 189 to provide at its output 190 a DC signal representing the directly measured difference in temperature between test and reference elements. Appropriate calibration or gain adjustment is provided by a potentiometer 192 which feeds a gain adjusted differential temperature signal to one input of a final differential amplifier 194. The latter subtracts the gain adjusted differential temperature signal from the corrosion signal on line 180 that is fed to its other input. Thus, a corrected corrosion signal, having both the primary and secondary temperature compensation, appears at the output 196 of differential amplifier 194.

It will be seen that making leads 156 and 158 of a material thermoelectrically different than the material of the probe test and reference elements enables these leads to perform two functions. The first function is their use in the AC measurement of probe element resistance. The second is the thermocouple measurement of temperature difference. The AC resistance measurement signal is processed via signal channels including AC amplifiers and DC eliminating filtering and phase sensitive demodulators to extract the amplitudes of the AC resistance signals. The thermocouple temperature difference signal, on the other hand, is handled in a DC channel, thus enabling its ready separation from the AC signals. Accordingly the two signals, the first being the corrosion signal with primary temperature compensation and the second being the temperature signal for secondary temperature compensation, are readily and differentially combined in the final amplifier 194.

In prior corrosion probes employing a resistance measurement principle and a reference element to minimize the temperature effects upon the measured resistance, it has been preferable, where a tubular test element is employed, to form the reference element of an adjoining section of the same tube from which the test element is made (to keep resistance-temperature coefficients of the two elements as nearly alike as possible) and to mount this reference element closely adjacent to and within the test element in the manner illustrated in FIG. 2. The cutting of a single tubular section into different sections, inserting one within the other, and thereafter carefully positioning and fixedly connecting the two has been preferred in an attempt to cause the test and reference elements to experience the same temperature, thereby affording improved primary temperature compensation. With the use of the secondary temperature compensation described herein, the precision of the primary compensation may be relaxed to some extent and such decrease in precision will itself be compensated by use of the described secondary compensation. Accordingly, different construction techniques and different structure may be employed to form a less costly probe, without loss of accuracy or precision overall compensation.

Thus, as illustrated in FIG. 7, the reference and test elements of a tubular probe may comprise a single integral length of tubing 200, fixed and sealed to an end plug 202 of a probe body 204. Tubular element 200 extends through the end plug 202, having a test element portion 206 located externally of the probe body 204 and having an integral internal reference element portion 210 positioned within the probe body 204. Leads 220, 222, 224, 226 and 228 are connected between probe connector terminals $A_2$, $B_2$, $C_2$, $D_2$ and $F_2$, respectively, and the indicated points on the test/reference element 200, at the end closure disc 208 for leads 220 and 222, at closure cap 202 for lead 224 at an inner portion of element 210 for lead 226, and at an inner portion of element 210 for lead 228. In this arrangement, lead 222, connected to terminal $B_2$, and lead 226, connected to terminal $D_2$, are the thermocouple leads, being of a thermoelectrically different material such as Constantan as previously described. Constantan lead 222 is connected to the test element at point 230, forming a first thermocouple junction, and Constantan lead 226 is connected to an innermost protected portion of reference element section 210 at point 232, forming a second thermoelectric junction with the steel of the probe element. The body of the probe and the tube 200 are filled, as previously described, with electrically insulative and thermally conductive potting compound such as Sauereisen cement. Electrical connections to the terminals $A_2$, $B_2$, $C_2$, $D_2$ and $F_2$ are the same as described in connection with the circuit of FIG. 6 for corresponding probe connected terminals of the wire probe of FIG. 5.

The simplified probe of FIG. 7 is much easier, faster, and less costly to manufacture and yet, because of the secondary temperture compensation, provides improved fidelity of corrosion measurement.

Although it is presently preferred to employ the described dual function thermoelectrically different leads for measurement of temperature difference, it will be readily appreciated that direct (or indirect) measurement of temperatures of test and reference elements, or of the difference of such temperatures, may be carried out, as previously mentioned, by any other appropriate temperature sensing arrangement, such as dual wire thermocouple junctions, thermistors, or separate resistance devices. Direct measurement of instantaneous temperature of test and reference elements may be made by dual measurement of resistances of the test and reference elements, the two resistance measurements (that for the primary corrosion measurement and temperature compensation, and that for secondary temperature compensation) being distinguished by use of such well known techniques as time sharing or use of different energizing frequencies. Secondary temperature compensation may be accomplished by either differential temperature sensing or by sensing of absolute temperature.

The foregoing detailed description is to be clearly understood as given by way of illustration and example only, the spirit and scope of this invention being limited solely by the appended claims.

What is claimed is:

1. In an electrical resistance type corrosion measuring instrument having test and reference elements in a probe adapted to be placed in an environment of which corrosive characteristics are to be measured, and having means for providing a corrosion signal representing corrosion of said test element, said signal having a primary temperature compensation for temperature of the environment of said probe elements, said elements having different thermal responses to temperature fluctuations of said environment, the improvement comprising apparatus for further compensating said signal for fluctuation of environment temperature, said apparatus comprising means for measuring temperatures of both said elements and generating a secondary temperature compensation signal representative of the temperature of said elements relative to each other, and means for combining said corrosion signal with said secondary temperature compensation signal to provide an output signal representative of corrosion of said test element and compensated for temperature fluctuation of said environment.

2. The apparatus of claim 1 wherein said elements have electrical resistances that vary with element size and temperature, said test element adapted to be exposed to said environment, said reference element being protected from said environment, said means for providing a corrosion signal comprising means for combining electrical signals indicative of resistances of said elements, said means for generating a secondary temperature compensation signal comprising means for generating first and second temperature signals indicative of temperature of said test and reference elements respectively, and means for differentially combining said temperature signals.

3. The instrument of claim 1 wherein said means for generating a secondary temperature compensation signal comprises means for directly sensing temperature difference between said test and reference elements and generating said secondary signal in accordance with the sensed difference.

4. The instrument of claim 1 wherein said means for generating a secondary temperature compensation signal comprises first temperature sensing means at said test element, second temperature sensing means at said reference element, and means responsive to said first and second temperature sensing means for generating a signal indicative of the difference of the sensed temperatures.

5. The instrument of claim 1 wherein said means for measuring temperatures and generating a secondary temperature compensation signal comprises a first lead connected to said test element and a second lead connected to said reference element, said leads being formed of a material that is thermoelectrically different than the material of said elements, and means for measuring the voltage difference between said leads to provide said secondary temperature compensation signal.

6. The instrument of claim 1 wherein said means for measuring temperatures and generating a secondary temperature compensation signal includes first and second thermoelectric junctions at said test and reference elements respectively.

7. A corrosion probe comprising a test element adapted to be exposed to an environment of which corrosive characteristics are to be measured, a reference element mounted adjacent said test element and protected from corrosion by said environment, resistance responsive means for generating a corrosion signal having a first compensation for temperature of said elements, means for measuring the difference in temperature between said test and reference elements, and means responsive to said temperature difference measuring means for compensating said corrosion signal for temperature differences of said test and reference elements.

8. The probe of claim 7 wherein said resistance responsive means comprises a first pair of electrical leads having said test element connected therebetween, a second pair of electrical leads having said reference element connected therebetween, means responsive to signals on said first and second pairs of leads respectively for generating test and reference resistance signals, and means for combining said resistance signals to provide a first corrosion signal, said means for measuring difference in temperatures comprising first and second ones of the leads of said first and second pairs, said first and second leads being formed of a material that is thermoelectrically different that the material of said probe elements to provide thermoelectric junctions between said probe elements and said first and second leads.

9. The corrosion probe of claim 7 wherein said means for measuring the difference in temperature between said test and reference elements comprises a first lead connected to said test element, and a second lead connected to said reference element, said leads being of a material thermoelectrically different than the material of said test and reference elements, and means for measuring the voltage differential between said leads.

10. The corrosion probe of claim 9 wherein said resistance responsive means for generating a corrosion signal includes one of said first and second leads.

11. In a corrosion probe having test and reference elements and means responsive to resistances of the elements for generating a primary corrosion signal having a primary compensation for temperature, the improvement comprising means for providing additional temperature compensation for said corrosion signal, said last mentioned means comprising
   first and second temperature sensing devices connected to sense temperatures of said test and reference elements respectively,
   means responsive to said devices for generating a secondary temperature compensation signal in accordance with the difference between sensed temperatures of said test and reference elements, and
   means for combining said temperature compensation signal with said primary corrosion signal.

12. The probe of claim 11 wherein at least one of said temperature sensing devices is a thermoelectric junction formed by a connection of a single thermoelectric wire to one of said test and reference elements.

13. The probe of claim 12 wherein the other of said sensing devices is a theromelectric junction formed by connection of a second single thermoelectric wire to the other of said elements, and wherein said means for generating said secondary temperature compensation signal comprises means for differentially combining signals on said first and second thermoelectric wires.

14. The probe of claim 11 wherein the means for generating a primary corrosion signal includes at least one pair of electrical wires connected to spaced portions of one of said elements and wherein one of said temperature sensing devices comprises one of the leads of said pair and its connection to said one element, said one lead being of a material thermoelectrically different than the material of said one element.

15. The method of providing temperature compensation of a corrosion probe of the type having a test element arranged for exposure to a corrosive environment, a reference element protected from the corrosive environment and means for measuring electrical parameters of the elements to obtain a corrosion signal indicative of corrosion of the test element, said method comprising
   sensing temperature of said test element,
   sensing temperature of said reference element,
   generating a signal representing the difference between the sensed temperatures, and
   employing said signal to compensate the corrosion signal.

16. The method of claim 15 wherein said steps of sensing temperature comprise establishing a thermoelectric junction at said test element, establishing a thermoelectric junction at said reference element, and measuring thermoelectric voltage between said junctions.

17. In a corrosion probe wherein a reference element protected from a corrosive environment is employed together with a test element to be placed in the corrosive environment, and wherein electrical parameters of the elements are measured to provide a corrosion signal compensated for changes in said electrical parameters caused by relatively static temperature of the corrosive environment, the method of providing further temperature compensation comprising the steps of
   directly sensing temperature of said test element,
   directly sensing temperature of said protected reference element, and
   employing the sensed temperatures to compensate said corrosion signal for temperature differences between said test and reference elements.

18. The method of claim 17 wherein said steps of sensing temperature comprise thermoelectrically producing a voltage difference between a point on said reference element and a point representative of temperature of said test element, and sensing said voltage difference.

* * * * *